United States Patent

Dubief et al.

[11] Patent Number: 6,132,707
[45] Date of Patent: Oct. 17, 2000

[54] TOPICAL COMPOSITION CONTAINING A SILICONE POLYMER WITH A POLYSILOXANE BACKBONE HAVING NON-SILICONE GRAFTS AND A FATTY-CHAIN AMPHIPHILIC POLYMER

[75] Inventors: Claude Dubief, Le Chesnay; Christine Dupuis, Paris, both of France

[73] Assignee: L'Oreal, Paris, France

[21] Appl. No.: 08/981,561

[22] PCT Filed: Sep. 16, 1996

[86] PCT No.: PCT/FR96/01436

§ 371 Date: Dec. 30, 1997

§ 102(e) Date: Dec. 30, 1997

[87] PCT Pub. No.: WO97/12586

PCT Pub. Date: Apr. 10, 1997

[30] Foreign Application Priority Data

Sep. 29, 1995 [FR] France .................................. 95 11482

[51] Int. Cl.⁷ ...................................................... A61K 7/06
[52] U.S. Cl. ..................... 424/78.08; 424/70.11; 424/70.12; 424/70.21; 424/70.22; 424/70.27; 424/70.31
[58] Field of Search ............... 424/70.12, 70.11, 424/70.21, 70.22, 70.27, 70.31, 78.08

[56] References Cited

U.S. PATENT DOCUMENTS 5,362,485  11/1994  Hayama et al. ........................... 424/70
5,855,878   1/1999  Coffindaffer et al. ................. 424/70.11

FOREIGN PATENT DOCUMENTS

| 0 412 705 | 2/1991 | European Pat. Off. |
| 0 524 612 | 1/1993 | European Pat. Off. |
| 0 582 152 | 2/1994 | European Pat. Off. |
| WO 91/15186 | 10/1991 | WIPO |
| WO 92/16179 | 10/1992 | WIPO |
| WO 95/00108 | 1/1995 | WIPO |
| WO 95/05800 | 3/1995 | WIPO |
| WO 95/06078 | 3/1995 | WIPO |

OTHER PUBLICATIONS

English Language Derwent Abstract of FR 2 709 955.

*Primary Examiner*—Michael A. Williamson
*Attorney, Agent, or Firm*—Finnegan, Henderson, Farabow, Garrett & Dunner, L.L.P.

[57] ABSTRACT

A cosmetic or dermatological composition for treating keratinous material, particularly human hair, including a cosmetically or dermatologically acceptable medium containing at least one silicone-grafted polymer with a polysiloxane backbone grafted by non-silicone organic monomers and at least one amphiphilic polymer comprising at least one fatty chain and at least one hydrophilic unit. Such compositions are particularly suitable for use as rinsable or non-rinsable products for washing and conditioning hair, hair setting or hair styling.

35 Claims, No Drawings

TOPICAL COMPOSITION CONTAINING A SILICONE POLYMER WITH A POLYSILOXANE BACKBONE HAVING NON-SILICONE GRAFTS AND A FATTY-CHAIN AMPHIPHILIC POLYMER

The present invention relates to a cosmetic or dermatological composition for treating keratin substances, in particular human hair, this composition comprising at least one grafted silicone polymer containing a polysiloxane skeleton grafted with non-silicone organic monomers and at least one amphiphilic polymer containing at least one fatty chain and at least one hydrophilic unit.

The polymers of the grafted silicone polymer type containing a polysiloxane skeleton grafted with non-silicone organic monomers are known in the prior art for their hairstyling properties. They are particularly advantageous in haircare cosmetics since they give the hair hold. However, when they are applied to the hair their cosmetic properties are unsatisfactory. It is observed that the hair has a coarse and crisp feel after these polymers have been applied, resulting from a non-continuous distribution of the polymer along the hair fibres.

The Applicant has observed that certain standard thickeners such as, for example, crosslinked poly(acrylic acid) homopolymers, used in haircare compositions containing these particular polymers have a tendency to lower the viscosity of the composition and do not allow the distribution of the composition along the wet or dry hair fibres to be improved appreciably, nor do they allow the softness to the touch or the disentangling properties to be improved appreciably after it has been applied.

The Applicant has found, surprisingly, that the use of an amphiphilic polymer containing at least one fatty chain and at least one hydrophilic unit, as a thickener in haircare compositions containing a polymer with a polysiloxane skeleton grafted with non-silicone organic monomers makes it possible not only to increase the viscosity of the medium of these compositions appreciably but also to improve, on application, the deposition of the grafted silicone polymer along the keratin fibres and to improve their cosmetic properties, especially as regards the feel and the disentangling, while at the same time retaining the styling properties of the grafted silicone polymer.

The composition according to the invention is thus essentially characterized in that it contains, in a cosmetically or dermatologically acceptable medium, at least one grafted silicone polymer containing a polysiloxane skeleton grafted with non-silicone organic monomers and at least one amphiphilic polymer containing at least one fatty chain and at least one hydrophilic unit.

In the following text, in accordance with what is generally accepted, the term silicone polymer is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

According to the present invention, the silicone polymer (s) which must be used is (are) those which comprise a main silicone chain (or polysiloxane ($\equiv$Si—O—$)_n$) on which is grafted, inside the said chain as well as, optionally, on at least one of its ends, at least one organic group containing no silicone.

These silicone polymers can be existing commercial products or can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of silicone polymers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) unsaturated carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo)polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth) acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate, or mixtures thereof.

One family of grafted silicone polymers which is particularly suitable for carrying out the present invention consists of silicone polymers containing in their structure the unit of formula (I) below:

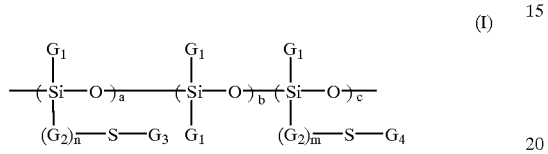

(I)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably of the isobutyl or methyl (meth)acrylate type.

Examples of silicone polymers corresponding to formula (V) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (I) are in particular polydimethylsiloxanes (PDMS) on which are grafted, via a thiopropylene-type connecting chain, polymer units of the polyisobutyl (meth)acrylate type.

Preferably, the number-average molecular mass of the silicone polymers of the invention, ranges approximately from 10,000 to 1,000,000 and even more preferably approximately from 10,000 to 100,000.

The grafted silicone polymer is preferably used in an amount ranging from 0.01 to 20% by weight relative to the total weight of the composition. More preferably, this amount ranges from 0.1 to 15% by weight and even more preferably from 0.5 to 10% by weight.

The amphiphilic polymers containing at least one fatty chain and at least one hydrophilic unit, which are used according to the invention, are preferably chosen from the group consisting of:

(1) holosides modified with groups containing at least one fatty chain;
    mention may be made, by way of example, of:
    celluloses or derivatives thereof, modified with groups containing at least one fatty chain, such as alkyl, arylalkyl or alkylaryl groups or mixtures thereof in which the alkyl groups are $C_8$–$C_{22}$;
    nonionic alkylhydroxyethylcelluloses such as the products Natrosol Plus Grade 330 CS and Polysurf 67 ($C_{16}$ alkyl) sold by the company Aqualon;
    quaternized alkylhydroxyethylcelluloses (cationic), such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda;
    nonionic nonoxynylhydroxyethylcelluloses, such as the product Amercell HM-1500 sold by the company Amerchol;
    nonionic alkylcelluloses, such as the product Bermocoll EHM 100 sold by the company Berol Nobel;
    poly($C_{12}$–$C_{18}$) alcohol saccharides, such as the product Emulsan (D-galactosamine/aminuronic acid mixture) and the product Biosan LPS-50 sold by the company Petroferm;
    hydroxypropylguars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhone-Poulenc;

(2) copolymers of maleic anhydride or of a derivative thereof and of monomers containing at least one fatty chain:
    mention may be made, by way of example, of:
    N-octadecyl vinyl ether/maleic anhydride copolymers, such as the product Gantrez AN-8194 sold by the company ISP;
    vinyl acetate/isobutyl monomaleate/vinyl neodecanoate terpolymers, such as the products ACV-4033 and 9649-147 sold by ISP, the product Meyprofix 509 sold by Meyhall and the products Densodrin BA and Lipoderm Liquor FP sold by BASF;

(3) polyurethanes and derivatives thereof containing groups containing at least one fatty chain, such as, for example, the following commercial products: Rheolate 205, 208 and 210 sold by the company Rheox; Bermodol Pur 2130 sold by the company Berol Nobel; Acrysol SCT-275, Acrysol RM-870 and Acrysol44, DW-1206 B, DW-1206 F, DW-1206 G and DW-1206 J sold by the company Rohm & Haas; Dapral T 212 sold by the company Akzo;

(4) copolymers of crotonic acid and of monomers containing at least one fatty chain;
    mention may be made, by way of example, of:
    vinyl acetate/crotonic acid/allyl stearate terpolymers;

(5) copolymers of N-vinylpyrrolidone and of monomers containing at least one fatty chain, such as olefins substituted with an alkyl radical containing a long hydrocarbon chain, such as, for example, the products Antaron V216 and Antaron V220 sold by the company ISP;

(6) copolymers of (meth)acrylic acid and of monomers containing at least one fatty chain; these monomers are chosen from fatty-chain hydrophobic monomers, amphiphilic monomers containing a fatty-chain hydrophobic portion and a hydrophilic portion, or mixtures thereof;

mention may be made, by way of example, of:

crosslinked copolymers of acrylic acid/$C_{10}$–$C_{30}$ alkyl acrylate, such as the products Pemulen TR 1, Pemulen TR 2, Carbopol 1382, Carbopol 1342 and Carbopol ETD 2020 sold by the company Goodrich;

(meth)acrylic acid/ethyl acrylate/alkyl acrylate copolymers, such as the product Acusol 823 sold by the company Rohm & Haas and the product Imperon R sold by the company Hoechst;

crosslinked acrylic acid/vinyl isodecanoate copolymers, such as the product Stabylen 30 sold by the company 3V;

acrylic acid/vinylpyrrolidone/lauryl methacrylate terpolymers, such as the products Acrylidone LM, ACP-1184 and ACP-1194 sold by the company ISP;

acrylic acid/lauryl (meth)acrylate copolymers, such as the product Coatex SX sold by the company Coatex;

(meth)acrylic acid/alkyl acrylate/polyethoxylated alkyl allyl ether terpolymers, such as the products Rheovis —CR, —CR$_3$, —CR$_2$ and —CRX sold by the company Allied Colloids;

methacrylic acid/ethyl acrylate/polyethoxylated stearyl allyl ether terpolymers, such as the products Salcare-SC90 and -SC80 sold by the company Allied Colloids (stearyl polyethoxylated with 10 mol of ethylene oxide, known as steareth-10);

methacrylic acid/ethyl acrylate/polyoxyethylenated lauryl acrylate terpolymers, such as the product Rheo 2000 sold by Coatex;

methacrylic acid/ethyl acrylate/polyoxyethylenated stearyl methacrylate terpolymers, such as the products Acrysol 22, Acrysol 25 and DW-1206A sold by the company Rohm & Haas;

methacrylic acid/ethyl acrylate/polyoxyethylenated nonylphenol acrylate copolymers, such as the product Rheo 3000 sold by Coatex;

acrylic acid/polyoxyethylenated stearyl monoitaconate copolymers or acrylic acid/polyoxyethylenated cetyl monoitaconate copolymers, such as the products 8069-72A and 8069-72B sold by National Starch;

methacrylic acid/butyl acrylate/hydrophobic monomer copolymers containing at least one fatty chain, such as the product 8069-146A sold by National Starch;

acrylic acid/$C_{15}$ alkyl acrylate/polyethylene glycol acrylate (28 mol of ethylene oxide) terpolymers, such as the product Dapral GE 202 sold by the company Akzo;

salts of a partial fatty acid ester of an acrylic acid/dimethylethanolamine copolymer, such as the product Dapral GE 202 DMA sold by the company Akzo;

acrylic acid/acrylate/amphiphilic monomer copolymers containing a fatty chain containing urethane groups, such as the product Additol VXW 1312 sold by Hoechst;

acrylic copolymers modified with fatty-chain hydrophobic groups, such as the product Acusol 102 sold by Rohm & Haas;

(7) nonionic copolymers of ($C_1$–$C_6$) lower alkyl (meth) acrylate and of amphiphilic monomers containing a fatty chain, such as, for example, copolymers of methyl methacrylate/ polyoxyethylenated stearyl acrylate, such as the product Antil 208 sold by the company Goldschmidt;

(8) nonionic copolymers of hydrophilic (meth)acrylates and of fatty-chain hydrophobic monomers, such as, for example, polyethylene glycol methacrylate/methyl methacrylate copolymers.

The amphiphilic polymers containing at least one fatty chain and hydrophilic units, according to the invention, are preferably used in an amount of between 0.01 and 20% by weight relative to the total weight of the composition. More preferably, this amount ranges from 0.1 to 15% by weight and even more preferably from 0.5 to 10% by weight.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and isopropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from fatty chain-free thickeners, fatty acid esters, fatty acid esters of glycerol, silicones, surfactants, fragrances, preserving agents, sunscreens, proteins, vitamins, polymers, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a foam.

These compositions are more particularly hairsetting lotions, blow-drying lotions, fixing compositions (lacquers) and styling compositions. The lotions can be packaged in various forms, in particular in vaporizers, pump-dispenser bottles or in aerosol containers in order to ensure application of the composition in vapourized form or in the form of a foam. Such packaging forms are indicated, for example, when it is desired to obtain a spray, a lacquer or a foam for fixing or-treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol foam, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for the non-therapeutic treating of keratin substances such as the hair, which consists in applying a composition as defined above to the hair and then optionally in rinsing with water.

The invention will now be illustrated more fully with the aid of the examples which follow, which should not be considered as limiting it to the embodiments described.

EXAMPLES

| EXAMPLE 1 Styling gel | |
|---|---|
| Grafted silicone polymer of formula (I) of polymethyl/methylsiloxane structure containing 3-propylthio polymethacrylic acid groups and 3-propylthio poly(methyl methacrylate) groups | 1 g AM |
| Oxyethylenated methacrylic acid/ethyl acrylate/stearyl methacrylate terpolymer (55/35/10) as an aqueous 30% dispersion sold under the name Acrysol 22 by the company Rohm & Haas | 1 g AM |
| Aminomethylpropanol, 100% neutralization of the said silicone polymer and of the terpolymer qs | |
| Demineralized water qs | 100 g |
| EXAMPLE 2 Styling gel | |
| Grafted silicone polymer of formula (I) of polymethyl/methylsiloxane structure containing 3-propylthio polymethacrylic acid groups and 3-propylthio poly(methyl methacrylate) groups | 2 g AM |
| Hydroxyethylcellulose modified with a cetyl chain, sold under the name Natrosol Plus Grade 330 S by the company Aqualon | 3 g AM |
| Aminomethylpropanol, 100% neutralization of the said grafted silicone polymer qs | |
| Demineralized water qs | 100 g |

COMPARATIVE VISCOSITY TESTS

The rheological properties of a standard thickener of the crosslinked poly(acrylic acid) homopolymer type, such as the product Synthalen K sold by the company 3V in an aqueous solution containing 1% by weight of this thickener and in an aqueous solution containing 1% by weight of this thickener and 1% by weight of grafted silicone polymer such as that described in Examples 1 and 2, are studied. The viscosities of the thickened solutions are measured using a Rheomat 180 machine fitted with the Contraves TV system.

The Theological properties of an amphiphilic polymer $P_i$ containing a fatty chain and at least one hydrophilic unit according to the invention in an aqueous solution containing 1% by weight of this thickening amphiphilic polymer and in an aqueous solution containing 1% by weight of this thickener and 1% by weight of grafted silicone polymer such as that described in Examples 1 and 2, are studied. In the following text, the index i is specific to the amphiphilic polymer studied.

All the solutions are neutralized to pH 7.5 with aminomethylpropanol.

The amphiphilic polymers according to the invention which were studied are as follows:

$P_1$: Oxyethylenated methacrylic acid/ethyl acrylate/stearyl methacrylate terpolymer (55/35/10) as an aqueous 30% dispersion, sold under the name Acrysol 22 by the company Rohm & Haas;

$P_2$: Methacrylic acid/ethyl acrylate/polyethoxylated stearyl allyl ether terpolymer Salcare-SC 90 sold by the company Allied Colloids (stearyl polyethoxylated with 10 mol of ethylene oxide, known as steareth-10);

$P_3$: Hydroxyethylcellulose modified with a cetyl chain, sold under the name Natrosol Plus Grade 330 S by the company Aqualon.

The viscosities of the solutions are indicated in centipoises in the following table:

| Polymer studied | Viscosity in cps of the aqueous solution containing 1% thickener alone or the grafted silicone polymer of Example 1 or 2 alone | Viscosity in cps of the aqueous solution containing 1% by weight of thickener and 1% by weight of grafted silicone polymer of Example 1 or 2 |
|---|---|---|
| Grafted silicone polymer of Examples 1 and 2 | 2.5 | no thickener |
| Crosslinked poly(acrylic acid) homopolymer | 7500 | 6500 |
| $P_1$ | 1700 | 6900 |
| $P_2$ | 75 | 1590 |
| $P_3$ | 360 | 700 |

It is observed that the crosslinked poly(acrylic acid) homopolymer in combination with the styling silicone polymer of the invention decreases the viscosity of the formulation, whereas the thickening amphiphilic polymers $P_i$ containing a fatty chain and at least one hydrophilic unit according to the invention substantially increase the viscosities of the solutions containing the grafted silicone polymer.

COMPARATIVE TESTS ON THE COSMETIC PROPERTIES

A sensory evaluation test was carried out on a panel of 5 individuals. The cosmetic criteria studied are the disentangling and softness to the touch after application to locks of wet, sensitized hair of the type SA 20. The three solutions A, B and C below are applied to each of these 5 individuals, on locks prewashed with shampoo, at a rate of 0.5 g per 5 g of lock:

Solution A containing 1% by weight of the grafted silicone polymer of Example 1 or 2

Solution B containing 1% by weight of the grafted silicone polymer of Example 1 or 2 and 1% by weight of the crosslinked poly(acrylic acid) homopolymer Synthalen K Solution C containing 1% by weight of the grafted silicone polymer of Example 1 or 2 and 1% by weight of the polymer $P_1$ as described above.

All the solutions are neutralized to pH 7.5 with aminomethylpropanol.

For each cosmetic criterion, the individuals tested award an evaluation grade from 0 to 5. The results of the tests are summarized in the table below.

| Solutions tested | Evaluation of the disentangling | Evaluation of the softness to the touch |
|---|---|---|
| A | 2 | 1.5 |
| B | 2.5 | 2.5 |
| C | 3.5 | 3.5 |

The 5 individuals interrogated considered that the presence of the thickening amphiphilic polymer containing a fatty chain and at least one hydrophilic unit, according to the invention, in solution C containing the grafted silicone polymer improved the softness of the hair to the touch and the disentangling of the hair when compared with solution A containing the grafted silicone polymer alone or solution B containing the said grafted silicone polymer in combination with the standard thickener of the crosslinked poly(acrylic acid) homopolymer type.

What is claimed is:

1. A cosmetic or dermatological composition comprising, in a cosmetically or dermatologically acceptable medium,
   (a) at least one grafted silicone polymer containing a polysiloxane skeleton grafted with at least one non-silicone organic monomer and
   (b) at least one amphiphilic polymer containing at least one fatty chain and at least one hydrophilic unit, wherein said at least one amphiphilic polymer is different from said at least one grafted silicone polymer,
   wherein said at least one grafted silicone polymer is selected from silicone polymers containing in their structure the unit of formula (I):

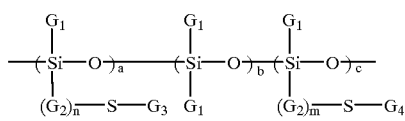

(I)

in which:
radicals $G_1$ each independently represent hydrogen or a $C_1$–$C_{10}$ alkyl radical or a phenyl radical;
radicals $G_2$ each independently represent a divalent $C_1$–$C_{10}$ alkylene group;
$G_3$ represents a polymer residue resulting from the (homo)polymerization of at least one anionic monomer containing ethylenic unsaturation;
$G_4$ represents a polymer residue resulting from the (homo)polymerization of at least one hydrophobic monomer containing ethylenic unsaturation;
m and n are equal to 0 or 1;
a is an integer ranging from 0 to 50;
b is an integer ranging from 10 to 350;
c is an integer ranging from 0 to 50;
with the proviso that one of a and c is not 0.

2. A cosmetic or dermatological composition according to claim 1, wherein said at least one grafted silicone polymer comprises a polysiloxane skeleton on which is grafted, inside said skeleton as well as, optionally, on at least one of its ends, said at least one non-silicone organic monomer.

3. A cosmetic or dermatological composition according to claim 1, wherein said at least one grafted silicone polymer is obtained by radical copolymerization between
   (a) at least one non-silicone organic monomer having ethylenic unsaturation selected from anionic and hydrophobic monomers, and,
   (b) at least one polysiloxane having, in its skeleton, at least one functional group capable of reacting with said ethylenic unsaturation of said at least one non-silicone monomer.

4. A cosmetic or dermatological composition according to claim 3, wherein said polysiloxane has several functional groups capable of reacting with said ethylenic unsaturation of said at least one non-silicone monomer.

5. A cosmetic or dermatological composition according to claim 3, wherein said at least one non-silicone anionic organic monomer is selected from linear and branched unsaturated carboxylic acids, optionally partially and totally neutralized in the form of a salt.

6. A cosmetic or dermatological composition according to claim 5, wherein said at least one non-silicone anionic organic monomer is selected from acrylic acid, methacrylic acid, maleic acid, maleic anhydride, itaconic acid, fumaric acid, crotonic acid, alkali-metal salts of the above acids, alkaline-earth metal salts of the above acids and ammonium salts of the above acids.

7. A cosmetic or dermatological composition according to claim 3, wherein said at least one non-silicone hydrophobic organic monomer is selected from acrylic acid esters of an alkanol and methacrylic acid esters of an alkanol.

8. A cosmetic or dermatological composition according to claim 7, wherein said alkanol is $C_1$–$C_{18}$.

9. A cosmetic or dermatological composition according to claim 8, wherein said alkanol is $C_1$–$C_{12}$.

10. A cosmetic or dermatological composition according to claim 3, wherein said at least one non-silicone hydrophobic organic monomer is selected from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate.

11. A cosmetic or dermatological composition according to claim 1, wherein said at least one grafted silicone polymer comprises, on the polysiloxane skeleton, at least one non-silicone organic group of anionic nature obtained by radical (homo)polymerization of at least one non-silicone anionic monomer of unsaturated carboxylic acid type, partially or totally neutralized in the form of a salt.

12. A cosmetic or dermatological composition according to claim 1, wherein said unit of formula (I) has at least one of the following characteristics:
   the radicals $G_1$ denote a $C_1$–$C_{10}$ alkyl radical;
   n is non-zero and the radicals $G_2$ represent a divalent $C_1$–$C_3$ radical;
   $G_3$ represents a polymeric residue resulting from the (homo)polymerization of at least one monomer of the carboxylic acid type containing ethylenic unsaturation; and
   $G_4$ represents a polymeric residue resulting from the (homo)polymerization of at least one monomer of the $C_1$–$C_{10}$ alkyl (meth)acrylate type.

13. A cosmetic or dermatological composition according to claim 1, wherein said unit of formula (I) simultaneously has the following characteristics:
   the radicals $G_1$ denote a methyl radical;
   n is 1 and the radicals $G_2$ represent a propylene radical;
   $G_3$ represents a polymeric residue resulting from the (homo)polymerization of at least one monomer selected from acrylic acid and methacrylic acid;
   $G_4$ represents a polymeric residue resulting from the (homo)polymerization of at least one monomer selected from isobutyl and methyl (meth)acrylate monomers.

14. A cosmetic or dermatological composition according to claim 1, wherein the number-average molecular mass of said at least one grafted silicone polymer ranges from 10,000 to 1,000,000.

15. A cosmetic or dermatological composition according to claim 14, therein said number-average molecular mass of said at least one grafted silicone polymer ranges from 10,000 to 100,000.

16. A cosmetic or dermatological composition according to claim 1, wherein said at least one grafted silicone polymer is present in a concentration ranging from 0.01 to 20% by weight relative to the total weight of said composition.

17. A cosmetic or dermatological composition according to claim 16, wherein said at least one grafted silicone polymer is present in a concentration ranging from 0.1 to 15% by weight relative to the total weight of said composition.

18. A cosmetic or dermatological composition according to claim 17, wherein said at least one grafted silicone polymer is present in a concentration ranging from 0.5 to 10% by weight relative to the total weight of said composition.

19. A cosmetic or dermatological composition according to claim 1, wherein said at least one amphiphilic polymer is selected from:

(a) holosides modified with groups containing at least one fatty chain;

(b) copolymers of maleic anhydride and derivatives thereof and of at least one monomer containing at least one fatty chain;

(c) polyurethanes and derivatives thereof containing groups containing at least one fatty chain;

(d) copolymers of crotonic acid and of at least one monomer containing at least one fatty chain;

(e) copolymers of N-vinylpyrrolidone and of at least one monomer containing at least one fatty chain;

(f) copolymers of (meth)acrylic acid and of at least one monomer containing at least one fatty chain;

(g) nonionic copolymers of ($C_1$–$C_6$) lower alkyl (meth) acrylate and of at least one amphiphilic monomer containing a fatty chain; and (h) nonionic copolymers of hydrophilic (meth)acrylates and of at least one fatty-chain hydrophobic monomer.

20. A cosmetic or dermatological composition according to claim 19, wherein said at least one monomer containing at least one fatty chain in (f) is selected from fatty-chain hydrophobic monomers and amphiphilic monomers containing a fatty-chain hydrophobic portion and a hydrophilic portion.

21. A cosmetic or dermatological composition according to claim 1, wherein said at least one amphiphilic polymer is present in a concentration ranging from 0.01 to 10% by weight relative to the total weight of the composition.

22. A cosmetic or dermatological composition according to claim 21, wherein said at least one amphiphilic polymer is present in a concentration ranging from 0.5 to 10% by weight relative to the total weight of the composition.

23. A cosmetic or dermatological composition according to claim 1, wherein said composition further comprises at least one additive selected from: fatty chain-free thickeners, fatty acid esters, fatty acid esters of glycerol, silicones, surfactants, fragrances, preserving agents, sunscreens, proteins, vitamins, different polymers, plant, animal, mineral and synthetic oils and any other suitable cosmetic additive.

24. A cosmetic or dermatological composition according to claim 1, wherein said cosmetically or dermatologically acceptable medium comprises water or a mixture of water and at least one cosmetically acceptable solvent.

25. A cosmetic or dermatological composition according to claim 24, wherein said at least one cosmetically acceptable solvent is selected from monoalcohols, polyalcohols, glycol ethers and fatty acid esters.

26. A cosmetic or dermatological composition according to claim 1, wherein said at least one grafted silicone polymer is dissolved in the cosmetically or dermatologically acceptable medium or is in the form of an aqueous dispersion of particles.

27. A cosmetic or dermatological composition according to claim 1, wherein said composition is a treatment composition for a keratin substance.

28. A cosmetic or dermatological composition according to claim 27, wherein said keratin substance is human hair.

29. A cosmetic or dermatological composition according to claim 1, wherein said composition is in the form of a gel, a milk, a cream, a thickened lotion or a foam.

30. A cosmetic or dermatological composition according to claim 1, wherein said composition is a styling product.

31. A cosmetic or dermatological composition according to claim 1, wherein said composition is a hair product to be applied before or after shampooing, dyeing, bleaching, permanent-waving or straightening the hair.

32. A cosmetic or dermatological composition according to claim 31, wherein said hair product is selected from shampoos and rinse-out and leave-in hair products.

33. A cosmetic or dermatological composition according to claim 1, wherein said composition is packaged in the form of a vaporizer, a pump-dispenser bottle or in an aerosol container.

34. A non-therapeutic process for treating a keratin substance comprising applying a composition according to claim 1 to said keratin substance, and then optionally rinsing with water.

35. A non-therapeutic process according to claim 34, wherein said keratin substance is human hair.

* * * * *